US008299126B2

(12) United States Patent
Cohen et al.

(10) Patent No.: US 8,299,126 B2
(45) Date of Patent: Oct. 30, 2012

(54) TREATMENT OF CANINE HEMANGIOSARCOMA WITH A HISTONE DEACETYLASE INHIBITOR

(75) Inventors: Leonard A. Cohen, Northampton, MA (US); Shantu Amin, Hershey, PA (US); Dhimant Desai, Hershey, PA (US)

(73) Assignees: Leonard A. Cohen, Northampton, MA (US); Shantu Amin, Hershey, PA (US); Dhimant Desai, Hershey, PA (US)

( * ) Notice: Subject to any disclaimer, the term of this patent is extended or adjusted under 35 U.S.C. 154(b) by 1413 days.

(21) Appl. No.: 10/547,396

(22) PCT Filed: Feb. 25, 2004

(86) PCT No.: PCT/US2004/005859
§ 371 (c)(1),
(2), (4) Date: Oct. 14, 2005

(87) PCT Pub. No.: WO2004/075859
PCT Pub. Date: Sep. 10, 2004

(65) Prior Publication Data
US 2006/0100286 A1 May 11, 2006

Related U.S. Application Data

(60) Provisional application No. 60/450,413, filed on Feb. 27, 2003.

(51) Int. Cl.
*A61K 31/16* (2006.01)
(52) U.S. Cl. .................................................. 514/575
(58) Field of Classification Search .................. None
See application file for complete search history.

(56) References Cited

U.S. PATENT DOCUMENTS

| 2,807,617 | A * | 9/1957 | Dalalian et al. | 544/360 |
| 7,154,002 | B1 * | 12/2006 | Bressi et al. | 562/623 |
| 2004/0018968 | A1 * | 1/2004 | Sgouros et al. | 514/9 |
| 2005/0065596 | A1 * | 3/2005 | Tseng et al. | 623/1.42 |

OTHER PUBLICATIONS

Clifford et al., "Treatment of Canine Hemangiosarcoma: 2000 and Beyond," 2000, J Vet Intern Med, vol. 14, pp. 479-485.*
1999, Chemoprevention of Carcinogen-Induced Mammary Tumorigenesis by the Hybrid Polar Cytodifferentiation Agent, Suberanilohydroxamic Acid (SAHA), Leonard A. Cohen et al., Cancer Research, vol. 19, pp. 4999-5005.
Sep. 15, 2000, Suberoylanilide Hydroxamic Acid, an Inhibitor of Histone Deacetylase, Suppresses the Growth of Prostate Cancer in Vitro and in Vivo, Lisa M. Butler, et al., Cancer Research, vol. 60, pp. 5165-5170.
2002, Suberoylanilide Hydroxamic Acid (SAHA), a Histone Deacetylase Inhibitor, Suppresses the Growth of Carcinogen-Induced Mammary Tumors, Leonard A. Cohen, et al., Anticancer Research, vol. 22, pp. 1497-1504.
2003, Chemopreventive Efficacy of Suberoylanilide Hydroxamic Acid (SAHA) Against 4-(Methylnitrosamino)-1-(3-pyridyl)-1-butanone (NNK)-induced Lung Tumorigenesis in Female A/J Mice, Dhimant Desai, et al., Anticancer Research, vol. 23, pp. 499-503.
1999, Structures of a histone deacetylase homologue bound to the TSA and SAHA inhibitors, Michael S. Finnin et al., Nature, vol. 401, pp. 188-193.
2001, The Histone Deacetylase Inhibitor Suberoylanilide Hydroxamic Acid Induces Differentiation of Human Breast Cancer Cells, Pamela N. Munster, et al., Cancer Research, vol. 61, pp. 8492-8497.
2003, Phase I clinical trial of histone deacetylase inhibitor: suberoylanilide hydroxamic acid administered intravenously, Kelly WK, et al., Clin. Cancer Research, vol. 9, pp. 3578-3588.
Mar. 15, 2010 "Veterinary Clinical Pathology Clerkship Program." Frankhauser et al. www.vet.uga.edu/vpp/clerk/frankhauser.
Jan. 1, 2003 "Hemangiosarcoma in dogs and cats." Annette N. Smith Vet Clin Small Anim vol. 33. pp. 533-552.
Jan. 1, 2001 "Miscellaneous Tumors." E.Gregory MacEwen. Small Animal Clinical Oncology. pp. 639-645.
Sutter, N.B., Ostrander, E.A., Dog Star Rising: The Canine Genetic System, Nat. Rev. Genet. 5(12) 900-910, 2004.
Ostrander, EA, Lindblad-Tok, Lander, E. Sequencing the Genome of the Domestic Dog , Canis Familiaris. White Paper submitted to the National Human Genome Res Inst, NIH, 2005.
FDA: First Drug to Treat Cancer in Dogs Approved, FDA News Release, US Food and Drug Administration, Jun. 3, 2009.
Telli, ML, Carlson, RW., First Line Chemotherapy for Metastatic Breast Cancer, Clin Breast Cancer, Jun. 9 Suppl 2 S66-72, 2009.
Gonzalez-Angulo, AM. Morales-Vasques, F, Hortobagyi, GN Overview of Resistance to Systemic Therapy in Patients with Breast Cancer, Adv. Exp. Med. Biol. 608: 1-22, 2007.
Modiano, JF, Ritt, MG, Breen M, Breen T., Canine Hemangiosarcoma—The Road from Despair to Hope. The Courier, Official Magazine of the Portuguese Water Dog Club of America, Jan. 2007.
Sorenmo, KU, Baez, JL, Clifford, CA et al., Efficacy and Toxicity of a Dose-Intensified Doxorubicin Protocol in Canine Hemangiosarcoma, J Vet. Intern Med. 18(2) 209-13, 2004.
Paxton, JW, The Allometric Approach for Interspecies Scaling of Phamacokinetics and Toxicity of Anti-Cancer Drugs, Clin. Exp. Pharmacol. Physiol. 22(11) 851-4, 1995.
Watanabe K.H., Bois, FY. Interspecies Extrapolation of Physiological Pharmacokinetic Parameter Distributions, Risk Analysis 16,(6) 741-54, 1996.
Downes, N. Revisiting Alternative Approaches to Assessment of Carcinogenic Risk. Toxicol. Pathol. 3892) 324-7, 2010.
Rohra, DK, Qazi, Y. Reliability of Rodent Models in Sourcebook of Models for Biomedical Research (Chapter 24) 213-217 2008 (Humana Press, NYC).
Werner, E. FDA Approves Cancer Treatment for Canines, Daily Hampshire Gazette, Jun. 4, 2009.
Cohen, L.A., Powers, B., Amin, S., and Desai, D, Treatment of canine haemangiosarcoma with suberoylanilide hydroxamic acid, a histone deacetylase inhibitor, Veterinary and Comparative Oncology, 2, 4, 243-248 (2004).

* cited by examiner

*Primary Examiner* — Daniel Sullivan
*Assistant Examiner* — Rachael E Bredefeld

(57) ABSTRACT

The present invention is directed to a method of treating cancer, particularly canine hemangiosarcoma. The method includes the continuous and regular administration of a formulation including a histone deacetylase inhibitor as part of the standard canine diet. The preferred histone deacetylase inhibitor is SAHA. The formulation is administered following splenectomy to prevent tumor recurrence.

9 Claims, No Drawings

TREATMENT OF CANINE HEMANGIOSARCOMA WITH A HISTONE DEACETYLASE INHIBITOR

FIELD OF THE INVENTION

The present invention is directed to a method of treating a canine with hemangiosarcoma with the administration of a histone deacetylase inhibitor, particularly suberoylanilide hydroxamic acid.

BACKGROUND OF THE INVENTION

Hemangiosarcoma (HSA) is a form of cancer originating in the endothelium, which is the lining of the heart, blood vessels, lymphatics, and spleen. HSAs have a predilection for the heart, pericardium and spleen. Due to their presence in internal organs, primary tumors are difficult to detect prior to the manifestation of clinical disease.

The direct cause of death due to HSA is disseminated intravascular coagulation, which causes the mammal to exhibit platelet deficiency, increased blood clotting times, decreased blood fibrin content, and increased fibrin degradation products. At present, there is no successful chemotherapeutic or radiation protocol for treatment of hemangiosarcoma (Clifford et al., J. Vet. Intern Med. 2000, 5:479). The average post-splenectomy survival time has been reported to be 49-120 days in canines. In fact, even with surgery and chemotherapy with doxorubicin, prognosis is less than six month once diagnosed in canines (Sorenmo et al., J Vet Intern Med 2000, 14(4):392-4).

A histone deacetylase inhibitor, such as SAHA (Richon et al., Proc. Natl. Acad. Sci. USA 1998, 95:3003), has been shown in cell culture and animal model studies to act as an anticancer agent (Marks et al., Curr. Opin. Oncol. 2001, 13:477). Subsequently, a series of studies was conducted in the N-nitrosomethylurea (NMU)-induced rat mammary tumor model using SAHA administered in the diet first as a chemopreventive agent and later as a chemotherapeutic agent (Cohen et al., Anticancer Res. 1999, 19: 4999-5006; Cohen et al., Anticancer Res. 2002, 22:1497-1504).

In 1999, it was found for the first time that SAHA could significantly inhibit the time of appearance, incidence, multiplicity and total number of NMU-induced rat mammary tumors, when added to the diet, with no deleterious side effects (Cohen et al., 1999). This was the first demonstration that SAHA could act as a chemopreventive agent in a solid (non-hematopoeitic) rat tumor. Further investigation showed that the presence of SAHA was required throughout the study period (Cohen et al., 2002). SAHA administered in the diet was found to decrease the size, slow the growth rate and, in some cases, induce the complete regression of established rat mammary tumors, again with no toxic side effects (Cohen et al., 2002). In addition, Butler et al. (Cancer Res. 2000, 60:5165) demonstrated that SAHA inhibited tumor growth of human prostate cancer cells in the mouse xenograft model.

Nonetheless, the data are not predictive for canines. Many cancers remain untreatable, and therapeutic approaches effective in one cancer often fail in another. Thus, there is a need in the art to treat certain aggressive forms of cancer and cancers that evade surveillance, and a need to adapt new therapies to treating otherwise untreatable tumors.

SUMMARY OF THE INVENTION

It has now been discovered in the present invention that administration of a histone deacetylase inhibitor has particularly effective anti-metastatic effects in dogs. The present invention thereby provides an advantageous method of treatment of canine cancers.

Accordingly, the invention provides a method of treating cancer in a canine in need thereof, comprising continuous administration of an effective amount of a histone deacetylase inhibitor.

In specific embodiments, the histone deacetylase inhibitor is selected from the group consisting of SAHA, trichostatin A, and butyrate. Preferably, the histone deacetylase inhibitor is SAHA.

In a preferred embodiment, the canine cancer is canine hemangiosarcoma.

In a specific embodiment, the administration is daily administration for an indefinite period of time after the diagnosis of cancer. Generally, administration of the histone deacetylase inhibitor continues for the life of the dog. Preferably, the administration is via the oral route.

In one embodiment, the dosage form comprises about 0.01 to about 100 mg/kg/day, more particularly about 0.05 to about 50 mg/kg/day, of the histone deacetylase inhibitor. Preferably, the dosage form comprises about 0.3 to about 30 mg/kg/day, and more particularly 1 to 5 mg/kg/day of the histone deacetylase inhibitor. More preferably still, the dosage is 3.3 mg/kg/day of the histone deacetylase inhibitor. In a specific embodiment, the histone deacetylase inhibitor is mixed as a powder with dog food. In another embodiment, it can be manufactured as a component of dog food.

In specific embodiments, the dog food is dry dog food, wet dog food, or mixtures thereof.

The invention also provides a method for prophylactic administration of a histone deacetylase inhibitor to prevent the dissemination of canine hemangiosarcoma comprising administration of an effective amount of a formulation of a histone deacetylase inhibitor to a canine on a continuous basis. Preferably the canine is aged.

The invention also provides a method for suppression of tumor growth associated with hemangiosarcoma in any mammal comprising the administration of an effective amount of a formulation of a histone deacetylase inhibitor to a mammal in need thereof.

The invention also provides for dietary administration of a food additive for the treatment of cancer comprising a histone deacetylase inhibitor and dog food. Preferably, the histone deacetylase inhibitor is SAHA.

These and other aspects of the invention are discussed more in the detailed description and examples.

DETAILED DESCRIPTION

The present invention advantageously provides a method of treatment of hemangiosarcoma, as well as various cancers, in canines. According to the invention, the administration of an effective amount of a histone deacetylase inhibitor on a continual basis prevents and inhibits metastasis. It also appears to inhibit tumorigenesis and may lead to tumor regression. The present invention not only significantly prolongs lifespan, but is also easy to administer and is nontoxic.

The present invention is based in part on a case study of a dog having hemangiosarcoma. In the case study, SAHA was administered to the dog at a dose of 100 mg per day (about 3.3 mg/kg/day) post-splenectomy, mixed as a dry powder in dog food. The dog remains in good health more than 400 days post-splenectomy.

The terms used in this specification generally have their ordinary meanings in the art, within the context of this invention and in the specific context where each term is used.

Certain terms are defined below to provide additional guidance in describing the compositions and methods of the invention and how to make and use them.

Treatment Groups

The compositions or unit dosage forms of the present invention may be administered to a canine, where the animal concomitantly has a form of cancer. In one embodiment, the composition is administered to inhibit tumor growth. In another embodiment, the composition is administered in the absence of overt evidence or diagnosis of a tumor for its protective effect. Since about 50% of all dogs over 10 years of age develop some type of tumor, this dietary additive can be used advantageously for its anti-tumor effects in this population.

In a preferred embodiment, the present invention is directed to treat a canine with cancer. In the preferred embodiment, the cancer is hemangiosarcoma. As used herein, the term "hemangiosarcoma" (HSA) refers to a cancer that originates in the endothelium. HSA may originate in any of the linings of the heart, blood vessels, lymphatics, and spleen. However, HSA has a predilection for the heart, pericardium and spleen. In addition to dogs, the invention contemplates treating hemangiosarcoma in any species using a histone deacetylase inhibitor especially SAHA.

In another embodiment of the present invention, other types of cancers occurring in canines are also targeted for treatment. Examples of types of canine cancers include, but are not limited to sarcomas, carcinomas, and adenocarcinomas. Cancers or malignant tumors are classified according to the type of tissue from which they originate. The broadest division of cancers separates the carcinomas, tumors which arise from epithelial tissues, and the sarcomas, which arise from all other tissues. Epithelium is tissue that covers the internal or external surfaces of the body. Thus, for example, skin, the lining of the mouth, stomach, intestines, and bladder are all epithelial tissue.

Within the category of carcinomas, there are many subdivisions corresponding to the types of different epithelium from which they may be derived. Therefore, the skin, which consists of a type of epithelium called squamous epithelium, can give rise to squamous cell carcinomas. There are other epithelial cells also present in the skin, basal cells, which give rise to basal cell carcinomas, and melanocytes, which give rise to melanomas.

Adenocarcinoma is a cancer originating in glandular cells. Adenocarcinomas occur in the lungs, from small glands in the bronchi; in the stomach from one of the several types of glands lining it; and in the colon, breast, ovaries, testes, prostate, lungs and in other locations. Adenocarcinomas arising from different organs can often be identified by the pathologist microscopically, even when they are removed from a different location where they may have metastasized, such as the liver. Thus, it is common to refer to an adenocarcinoma of the stomach which has metastasized to the liver, or one from the colon which has metastasized to the lungs.

As used herein, the term "tumorigenesis" refers to the neoplastic process leading to the appearance of a tumor. In the present invention, the inhibition of tumor growth is related not to toxicity but to differentiation of the tumor cells toward a normal phenotype.

As used herein, the term "metastasis" refers to the movement via the circulatory system of a disease-producing agent (such as cancer cells) from an original site of disease to another part of the body with development of a similar lesion in the new location.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

Histone Deacetylase Inhibitor

As used herein, the term "histone deacetylase inhibitor" refers to various classes of anticancer compounds. These compounds include, but are not limited to, hydroxamic acids such as SAHA (suberoylanilide hydroxamic acid); trichostatins including trichostatin A, oxamflatin, ABHA, scriptaid, pyroxamide, and propenamide; short-chain fatty acids such as butyrate, valproate, and phenylbutyrate; epoxyketone-containing cyclic tetrapeptides such as the trapoxins, HC-toxin, chlamydocin, diheteropeptin, WF-3161, Cy-1 and Cy-2; non-epoxyketone-containing cyclic tetrapeptides such as FR901228, apicidin, and cyclic-hydroxamic-acid-containing peptides; benzamides such as MS-27-275, CI-994, and benzamide analogs; depudecin; and organosulfur compounds. In one embodiment of the present invention, the compounds administered in the present invention are hydroxamic acids. Preferably, the hydroxamic acid is SAHA. In another embodiment, the compounds administered in the present invention are short chain fatty acids. For example, the short chain fatty acid may be butyrate.

SAHA, a cytodifferentiating agent, is a phenylamide derivative having the following chemical structure:

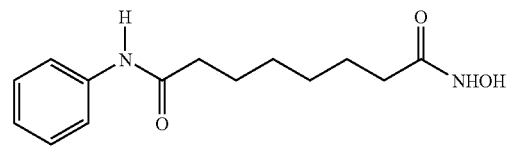

SAHA can be prepared by chemical synthesis, such as the method of Desai et al., J. Labelled Cpd. Radiopharm 2000, 43:229-336, incorporated herein by reference. The monoethyl ester of subaryl chloride is condensed with aniline in presence of triethylamine to give the anilide derivative in 92% yield. This anilide on treatment with methanolic hydroxylamine hydrochloride in the presence of sodium methoxide gives SAHA in 94% yield Like SAHA, Trichostatin A (TSA) is also a hydroxamic acid:

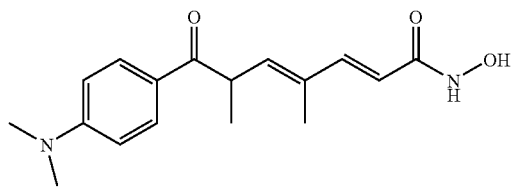

TSA, an antifungal antibiotic, is a specific inhibitor of mammalian histone deacetylase.

TSA inhibits the eukaryotic cell cycle by blocking cell progression at the G1 phase. TSA also induces morphological reversion of transformed cells. TSA is readily available from various chemical manufacturers, e.g., Sigma Aldrich (St. Louis, Mo.).

Butyrate, a short chain fatty acid, also acts as a histone deacetylase inhibitor in the same manner as TSA. Butyrate is readily available from various chemical manufacturers, e.g., Sigma Aldrich.

Formulation

The present invention also provides formulations containing therapeutic agents of the invention, which formulations are suitable for administration to treat or prevent cancer and its consequences, e.g., for the treatment and prevention of metastasis.

Suitable preparations of such compositions include emulsions or solid forms suitable for emulsion. As used herein "solid forms" include powders and finely divided particles. Due to the insoluble nature of the active compound, e.g., SAHA, the preferred preparation is in the form of a powder. The active compounds of the present have proven to be very stable at room temperature.

For oral administration, the therapeutics can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The preparations can also contain buffer salts, flavoring, coloring and sweetening agents as appropriate.

The phrase "pharmaceutically acceptable" refers to molecular entities and compositions that are "generally regarded as safe" (GRAS), e.g., that are physiologically tolerable and do not typically produce an allergic or similar untoward reaction, such as gastric upset, dizziness and the like, when administered to an animal. Preferably, as used herein, the term "pharmaceutically acceptable" means approved by a regulatory agency of the Federal or a state government or listed in the U.S. Pharmacopeia or other generally recognized pharmacopeia for use in animals.

The term "carrier" refers to a diluent, adjuvant, excipient, or vehicle with which the compound is administered. Such pharmaceutical carriers can be sterile liquids, due to its high insolubility in water, oils, including those of petroleum, animal, vegetable or synthetic origin, such as peanut oil, soybean oil, mineral oil, sesame oil and the like. The histone deacetylase inhibitor can be suspended in oil. Carriers such as micelles or dextrans can be used to deliver the agent in an aqueous solution or suspension. Suitable pharmaceutical carriers are described in "Remington's Pharmaceutical Sciences" by E. W. Martin.

Many methods may be used to introduce the formulation of the invention; these include but are not limited to oral, intradermal, intramuscular, intraperitoneal, intravenous, subcutaneous, intranasal routes, and via scarification (scratching through the top layers of skin, e.g., using a bifurcated needle) or any other standard routes of administration. Preferably, the oral route of administration is used.

The present invention's formulation includes the histone deacetylase inhibitor in amounts based upon the weight of the canine. For example, the amount administered can range from about 0.05 to about 50 mg/kg/day. More preferably, the amount is about 0.3 to about 30 mg/kg/day, and more particularly 1 to 5 mg/kg/day of the histone deacetylase inhibitor. More preferably still, the dosage is about 3.3 mg/kg/day. In a specific embodiment, the histone deacetylase inhibitor is mixed as a powder with dog food. In another embodiment, it can be manufactured as a component of dog food.

In a preferred embodiment, the histone deacetylase inhibitor is mixed with a standard serving of dog food for consumption. As used herein, the standard serving is a veterinarian-accepted standard for canine diet. The dog food may be wet, dry, or combination thereof. Any veterinarian-accepted form of dog food can be used. In addition, additional ingredients may be added including but not limited to vitamins, including but limited to brewers yeast, and lipids, including but not limited to essential fatty acid mixtures.

Alternatively, the histone deacetylase inhibitor, particularly, SAHA, can be included as dietary additive ingredient in commercial dog food, whether wet or dry. Such a dog food is particularly suitable for aged dogs, e.g., dogs at least about 10 years old.

Administration

The compound, pharmaceutical composition, or unit dosage form of the present invention may be administered alone at appropriate dosages defined by routine testing in order to obtain optimal activity while minimizing any potential toxicity.

The daily dosage of the compound of the present invention may vary according to a variety of factors such as underlying disease states, the individual's type, species, and medical condition, weight, sex, age, the severity of the condition to be treated; the route of administration; and the particular compound thereof employed. Advantageously, SAHA has demonstrated almost no measurable toxicity other than possible fatigue at high doses. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves consideration of the absorption, distribution, metabolism, and excretion of a drug, which are readily quantified.

The pharmaceutical composition or unit dosage form may be administered in a single daily dose, or the total daily dosage may be administered in divided doses of two, three or four times daily. Preferably, the composition or dosage form is administered in the food of the animal in need of treatment on a daily basis. In other embodiments, the administration of the dosage regime may be every other day, perhaps every third day. In addition, using delayed release formulations would provide for alternative dosage regimens.

In addition, co-administration or sequential administration of other active agents may be desirable. For combination treatment with more than one active agent, where the active agents are in separate dosage formulations, the active agents can be administered concurrently, or they each can be administered at separately staggered times. The dosage amount may be adjusted when combined with other active agents as described above to achieve desired effects. On the other hand, unit dosage forms of these various active agents may be independently optimized and combined to achieve a synergistic result wherein the pathology is reduced more than it would be if either active agent were used alone.

According to the present invention, the administration must be continuous and regular to sustain the anti-metastatic effects of the formulation. In the preferred embodiment, the administration extends indefinitely.

The formulation of the present invention is to be administered at any point pre-diagnosis as a prophylactic to tumor development, and preferably post-splenectomy to inhibit metastasis. In the present invention, the lifespan of the patient is prolonged greater than the 80 days median survival, preferably greater than 400 days, most preferably greater than 500 days.

As used herein, the "prolonged life span" is in relation to the prognosis of the cancer only.

Clinical Benefits and Uses

The present invention provides a first-time treatment regime for animal cancers, particularly canine hemangiosarcoma. The present regimen can be used, not only to prolong life of the animal by inhibiting metastasis, but also as a formulation against recurrence of tumors associated with the cancer. Additionally, the present invention promotes tumor regression and a normal hematologic profile. With the administration of the composition, the animal will not experience weight loss, and will have improved coat texture. Also, the administration of histone deacetylase inhibitors is without neurological symptoms.

The SAHA compound is easy to administer as it has no offensive smell and no taste, and is stable at room temperature. Furthermore, the compound is not readily metabolized by the animal. In fact, analyzed urine output indicates that SAHA is rapidly removed from the body and has a short half-life of approximately three to four hours. The present invention has been shown to inhibit metastasis of the cancer, which is directly associated with the vascular endothelial system. Therefore, it may be possible with further studies to better understand the effect of SAHA on the vascularization of tumors, not only in canines, but perhaps in humans as well.

EXAMPLES

The present invention will be better understood by reference to the following Examples, which are provided as exemplary of the invention, and not by way of limitation.

Example 1

Treatment of Canine Hemangiosarcoma with SAHA, A Histone Deacetylase Inhibitor

This example presents a case report of treatment of canine hemangiosarcoma with a histone deacetylase inhibitor.

Clinical Presentation

A 75 pound (33.75 kg), 12 year old female Rhodesian Ridgeback-Pit Bull mix was diagnosed with hemangiosarcoma. Symptoms included unexplained weakness, pale color to the mucous membranes of the mouth, lack of appetite and excessive consumption of water. The dog was brought to an emergency veterinary center, where X-ray and sonogram examination indicated a multi-lobulated mass on the spleen. An emergency splenectomy was performed, during which approximately 1 liter of blood was aspirated from the body cavity. There was no gross evidence of metastases in the liver or heart and a liver biopsy was taken. Histopathological examination revealed a tumor mass in the spleen consisting of spindle cells forming solid masses as well as irregular vascular channels filled with blood. Nuclei were mildly pleomorphic, oval and had prominent nucleoli. Mitoses were occasionally present. Extramedullary hematopoiesis was present throughout and large areas of hemorrhage and necrosis was typical. The tumor was multifocal throughout the spleen. Pathology results were reported as hemangiosarcoma, grade 1, spleen, with a normal liver.

Treatment Protocol

Starting approximately 2 weeks after splenectomy, when signs of weakness had re-appeared, SAHA was administered in the diet at 100 mg/day, 7 days/week. The dose was based on a rough extrapolation from rat studies. The diet consisted of a cup of standard pelleted dog food (Solid Gold, Hund-n-Flocken), a teaspoonful of brewers yeast (Foster and Smith, Rhinelander, Wis.), 1-2 ml of an essential fatty acid mixture containing n-6 and n-3 PUFA (Foster and Smith), and 2 tablespoonfuls of wet dog food (Pedigree®, Kal Kan Foods, Inc., CA), in which the SAHA was administered.

The monoethyl ester of subaryl chloride was condensed with aniline in presence of triethylamine to give the anilide derivative in 92% yield. This anilide on treatment with methanolic hydroxylamine hydrochlordie in presence of sodium methoxide gave SAHA in 94% yield.

Within 24 hrs, there was an immediate, observable decrease in weakness and lethargy. The dog became active, alert and showed no signs of weakness or abnormal eating or drinking patterns. For three months from diagnosis, the dog went through periods of high alertness and activity punctuated by brief periods of mild lethargy. The dose of SAHA was increased to 110 mg/day and since that time, the dog has shown no signs of decreased energy.

Follow-Up Examinations

Approximately one month post-splenectomy, the dog was examined and found to be in good condition. A blood test revealed blood chemistries in the normal range, with the exception of LDH that was slightly out-of-range, 49 (reference range, 50-550). Hematology analysis revealed normal ranges for all parameters except two, namely, RBC, 4.96 (range, 5-8) and hemoglobin, 13.2 (range, 14-21), which were only slightly below normal levels. The platelet count was above the normal range 550, (reference range, 100-450). It is of interest that at a routine examination two months before the splenectomy, a blood chemistry revealed a low reading for LDH 43 (reference range, 50-550), hence, the low LDH levels were present prior to the clinical appearance of hemangiosarcoma.

A little over 7 months post-splenectomy, the dog was examined for possible signs of metastasis by chest X-Ray, abdominal ultrasound, echogram, urinalysis and CBC. It was reported that "all diagnoses are unequivocal, no evidence of dissemination of the original (hemangiosarcoma) neoplasm". Blood chemistry analysis revealed all normal values, with the exception of a low alkaline phosphatase, 3 (reference range 10-150), RBC, 4.98 (range 5.5-8.5), and Hematocrit, 35.3 (range 37-55); and a high, segmented neutrophil, 36.5 (range, 32-36) and bands neutrophils, 6 (range, 0-3). These results provide evidence that SAHA suppressed the metastatic dissemination of neoplastic endothelial cells for 210 days post-splenectomy.

The dog remains in good health 400 days post-splenectomy. This result surpasses that of reported survivorship in dogs treated with chemotherapy (Clifford et al., J. Vet. Intern.

Med 2000, 5:479). Post-splenectomy SAHA therapy has the added advantage that it is administered orally in the home settings, requires no expensive hospital visits, and has none of the deleterious side effects of chemotherapy.

Conclusion

In summary, evidence is presented that oral administration of the HDAC inhibitor SAHA, on a daily basis, provides a viable non toxic treatment for preventing the dissemination of vasoformative tumors such as canine hemangiosarcoma.

Without intending to limit the present invention to any particular theory not specifically recited in the claims, at this point in time, one can only speculate as to the mechanism underlying the metastasis-suppressing effect of SAHA on disseminated hemangiosarcoma. It is known that the eukaryotic genome is organized into chromatin fibers and that higher order folding of chromatin, controlled by histone modifying enzymes, such as HDAC, may be central to transcriptional control (Horn and Peterson, Science 2002, 297:1824). The importance of histones lies in the fact that the building block of chromatin, the nucleosome, consists of 147 base pairs of DNA wrapped around a core histone octamer consisting of histones H2A, H2B, H3, and H4 in addition to the core histones there also are linker histones, such as H1, which link nucleosomes to one another. It has been shown that moderate to high levels of histone acetylation destabilize the folding of nucleosomal arrays and this correlates with enhanced transcriptional elongation by RNA polymerase. In contrast, transcriptional repression, induced by histone deacetylases, stabilizes folding by deacetylation of the NH2 terminal histone tails (Wolffe and Guschin, Struct. Biol. 2000, 129:102). In general, deacetylated histones are associated with increased cell proliferation and hyperacetylated histones are associated with cell growth arrest, differentiation and/or apoptosis (Marks et al., Curr. Opin. Oncol. 2001, 13:477). Hence, by blocking the removal of acetyl groups, one can hypothesize that SAHA increases the acetylation level of histones and thereby increases genomic transcription in transformed endothelial cells. The increase in gene transcription may involve turning on tumor suppressor genes, such as p53, induction of cell differentiation, or tumor cell apoptosis—all of which possibilities remain to be proven. Alteration of proteins involved in metastasis such as actin, tubulin (Maruta et al, J. Cell Biol. 2001, 103:571), vascular endothelial growth factor (VEGF) (Kim et al., Nat. Med. 2001, 7:437) or neoangiogenesis (Deroanne et al., Oncogene 2002, 21:427,), may also play a role in SAHA's effect. A recent report by Suenoga et al. (Int J Cancer 2002, 97:621) indicating that HDAC inhibitors suppress telomerase activity in prostate cancer cells, is of interest since increased telomerase activity is closely associated with tumor cell proliferation. Future studies may determine whether SAHA prevents metastatic dissemination of hemangiosarcoma by acting as a telomerase inhibitor specific to endothelial cells.

Example 2

Clinical Evaluation of HSA and SAHA in a Canine Population

The present study evaluates the efficacy of the administration of SAHA in a canine population diagnosed with HSA. Specifically, 30 dogs diagnosed with HSA and requiring splenectomy are included in the present study. The control group consists of 15 dogs receiving placebo. The test group consists of 15 dogs receiving SAHA administered daily in their food. The amount of SAHA is administered based upon the weight of the dog, approximately 3-5 mg/kg/day. Administration begins 7 days post-splenectomy and continues indefinitely. The number of survival days upon administration of SAHA is calculated and compared between placebo and test groups.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed is:

1. A method of treating canine hemangiosarcoma in a canine in need of such treatment, wherein the treatment consists of orally administering to the canine in need thereof an effective amount of a histone deacetylase inhibitor that is a hybrid-polar hydroxamic acid.

2. The method of claim 1, wherein the hybrid-polar hydroxamic acid is suberoylanilide hydroxamic acid.

3. The method of claim 1, wherein said oral administering comprises daily administration of said histone deacetylase inhibitor that is a hybrid-polar hydroxamix acid after a diagnosis of canine hemangiosarcoma in said canine.

4. The method of claim 1, wherein said administering comprises orally administering said histone deacetylase inhibitor that is a hybrid-polar hydroxamic acid to said canine in an amount of about 0.3 to about 30 mg/kg/day.

5. The method of claim 4, wherein said histone deacetylase inhibitor that is a hybrid-polar hydroxamic acid is administered to said canine in amount of about 1 mg/kg/day to 5 mg/kg/day.

6. The method of claim 5, wherein said administering comprises administering said histone deacetylase inhibitor that is a hybrid-polar hydroxamic acid to said canine in an amount of about 3.3 mg/kg/day.

7. The method of claim 4, wherein the histone deacetylase inhibitor that is a hybrid-polar hydroxamic acid is administered as an admixture with wet dog food, dry dog food, or a mixture of wet and dry dog food.

8. The method of claim 4, wherein the histone deacetylase inhibitor that is a hybrid-polar hydroxamic acid is suberoylanilide hydroxamic acid.

9. The method of claim 1 wherein the canine hemangiosarcoma is canine spleenic hemangiosarcoma.

* * * * *